(12) United States Patent
Jung

(10) Patent No.: US 9,784,091 B2
(45) Date of Patent: Oct. 10, 2017

(54) SYSTEMS AND METHODS FOR MEASURING BENDING, WEIGHT ON BIT AND TORQUE ON BIT WHILE DRILLING

(71) Applicant: Sebastian Jung, Lower Saxony (DE)

(72) Inventor: Sebastian Jung, Lower Saxony (DE)

(73) Assignee: BAKER HUGHES INCORPORATED, Houston, TX (US)

( * ) Notice: Subject to any disclaimer, the term of this patent is extended or adjusted under 35 U.S.C. 154(b) by 0 days.

(21) Appl. No.: 15/047,921

(22) Filed: Feb. 19, 2016

(65) Prior Publication Data
US 2017/0241254 A1  Aug. 24, 2017

(51) Int. Cl.
| | |
|---|---|
| G01B 11/16 | (2006.01) |
| E21B 47/00 | (2012.01) |
| E21B 10/00 | (2006.01) |
| G01N 3/20 | (2006.01) |
| G01L 1/24 | (2006.01) |
| G01L 3/00 | (2006.01) |

(52) U.S. Cl.
CPC .......... E21B 47/0006 (2013.01); E21B 10/00 (2013.01); E21B 47/00 (2013.01); G01B 11/16 (2013.01); G01L 1/24 (2013.01); G01L 3/00 (2013.01); G01N 3/20 (2013.01)

(58) Field of Classification Search
CPC .... G02B 1/043; G02B 6/4405; G02B 6/4413; G02B 6/4434; F16C 41/007; F16C 19/522; F16C 2208/34; F16C 2229/00; F16C 2240/14; F16C 33/585; F16C 41/00; F16C 41/008; G01B 15/06; G01N 11/14
See application file for complete search history.

(56) References Cited

U.S. PATENT DOCUMENTS

| | | |
|---|---|---|
| 4,291,978 A | 9/1981 | Seigel |
| 4,347,748 A | 9/1982 | Pierson |
| 4,821,563 A | 4/1989 | Maron |
| 5,386,724 A | 2/1995 | Das et al. |
| 5,705,810 A | 1/1998 | Wang et al. |
| 6,587,211 B1 | 7/2003 | Gelbart |
| 6,948,381 B1 | 9/2005 | Discenzo |
| 7,586,083 B2 | 9/2009 | Vahabzadeh et al. |
| 7,757,552 B2 | 7/2010 | Bogath et al. |
| 7,889,332 B2 | 2/2011 | Omichi et al. |
| 7,973,914 B2 | 7/2011 | Omichi et al. |
| 8,171,805 B2 | 5/2012 | Stevens |
| 8,587,780 B2 | 11/2013 | Gallet et al. |

(Continued)

OTHER PUBLICATIONS

"Drilling Dynamics Sensors and Optimization"; 2010 Schlumberger; www.slb.com/drilling; 16 pgs.

Primary Examiner — Michael P Stafira
(74) Attorney, Agent, or Firm — Cantor Colburn LLP

(57) ABSTRACT

An apparatus for determining torque on bit and bending forces in a drilling assembly. The apparatus includes a body having an inner bore defined by an inner wall and having an outer wall, the body also including first and second light bores disposed between the inner wall and the outer wall and a light emitting assembly arranged and configured to cause a light beam to enter the first and second light bores. The assembly further includes first and second light sensors disposed in or at an end of the first and second light bores, respectively, that measure a location where light that enters the first and second light bores contacts the sensors.

20 Claims, 7 Drawing Sheets

(56) References Cited

U.S. PATENT DOCUMENTS

| | | | |
|---|---|---|---|
| 8,833,183 B2 | 9/2014 | Blessum et al. | |
| 8,833,487 B2 | 9/2014 | Krueger et al. | |
| 8,943,905 B2 | 2/2015 | Theiss et al. | |
| 2007/0242265 A1* | 10/2007 | Vessereau | E21B 47/0002 356/241.1 |
| 2011/0308332 A1* | 12/2011 | Blessum | G01L 1/24 73/862.624 |
| 2014/0137638 A1* | 5/2014 | Liberzon | G01N 11/14 73/54.28 |
| 2014/0231141 A1 | 8/2014 | Hay et al. | |
| 2014/0260676 A1 | 9/2014 | Janik et al. | |
| 2015/0021093 A1 | 1/2015 | Clark et al. | |
| 2015/0160082 A1 | 6/2015 | Khoraych et al. | |

* cited by examiner

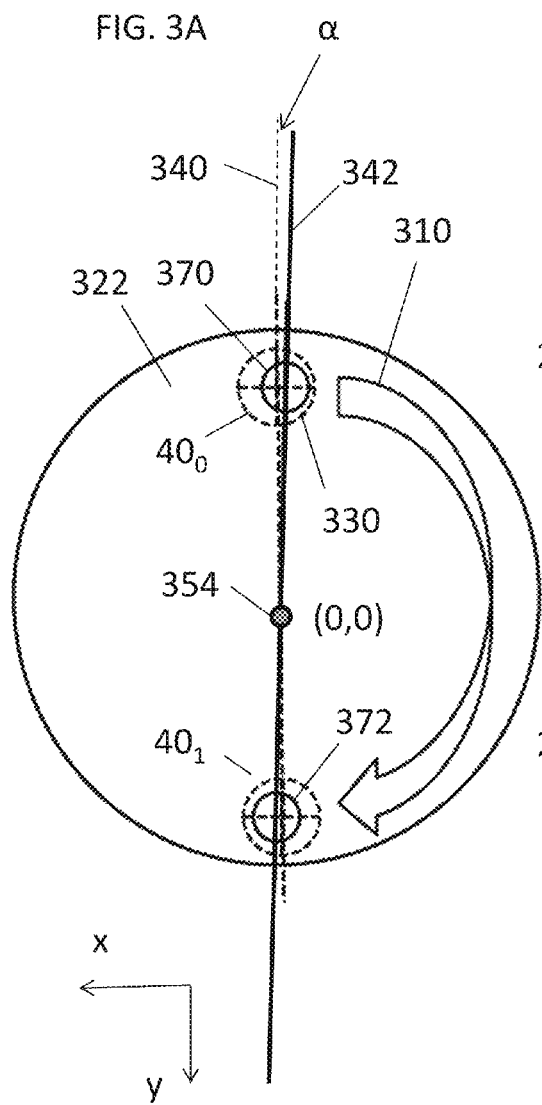
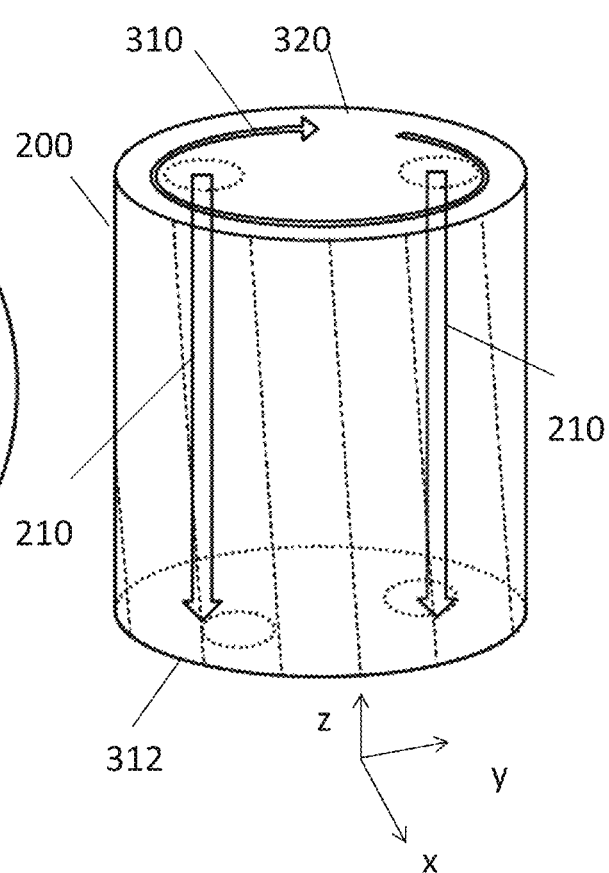

US 9,784,091 B2

SYSTEMS AND METHODS FOR MEASURING BENDING, WEIGHT ON BIT AND TORQUE ON BIT WHILE DRILLING

BACKGROUND

During drilling operations, sensors are often utilized to measure various forces exerted on a drill string. Exemplary forces include weight-on-bit (WOB), toque-on-bit (TOB) and bending loads/forces on various parts of the drill string. These forces can affect the dynamic behavior of the drill string, and if not monitored, can result in damage to downhole components or compromised operation. Such measurements provide information that can be used to, for example, measure drilling parameters or monitor downhole conditions.

Commonly WOB, TOB and bending loads on a drill strings are measured by strain gauges. The most common type of strain gauge consists of an insulating flexible backing which supports a metallic foil pattern. As the object is deformed, the foil is deformed, causing its electrical resistance to change. This resistance change, usually measured using a Wheatstone bridge, is related to the strain by the quantity known as the gauge factor.

SUMMARY

Disclosed herein is an apparatus for determining torque on bit and bending forces in a drilling assembly. The apparatus includes a body having an inner bore defined by an inner wall and having an outer wall, the body also including first and second light bores disposed between the inner wall and the outer wall and a light emitting assembly arranged and configured to cause a light beam to enter the first and second light bores. The assembly further includes first and second light sensors disposed in or at an end of the first and second light bores, respectively, that measure a location where light that enters the first and second light bores contacts the sensors.

Also disclosed is a method form measuring, while drilling torque on bit and bending forces in a drilling assembly. The method includes: providing light beams through at least a portion of first and second light bores in a body having an inner bore defined by an inner wall and having an outer wall, the first and second light bores formed between the inner wall and the outer wall; sensing a location on sensors disposed in or at an end of the first and second light bores, respectively, where light that enters the first and second light bores contacts the sensors; and comparing the sensed locations with reference locations to determine at least one of torque on bit and bending forces in the assembly.

Also disclosed is an apparatus for determining weight on bit in a drilling assembly. The apparatus includes a body having an inner bore defined by an inner wall and having an outer wall, the body also including a light bore disposed between the inner wall and the outer wall and a light emitting assembly that includes a light source, a sensor, a beam splitter, and a wall having a slit disposed between the light source and the sensor, the light emitting assembly arranged and configured to cause a light beam to enter the light bore. The assembly also includes a mirror disposed in or at an end of the light bore that reflects light back into the light emitting assembly. In this embodiment, the beam splitter causes a portion of the reflected light to be directed towards the slit in the wall to contact the sensor.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings, wherein like elements are numbered alike, in which:

FIGS. 3a and 3b show from top and perspective view, respectively, the effect of torque on light beam locations in an exemplary assembly of FIG. 2;

DETAILED DESCRIPTION

Figure 1:
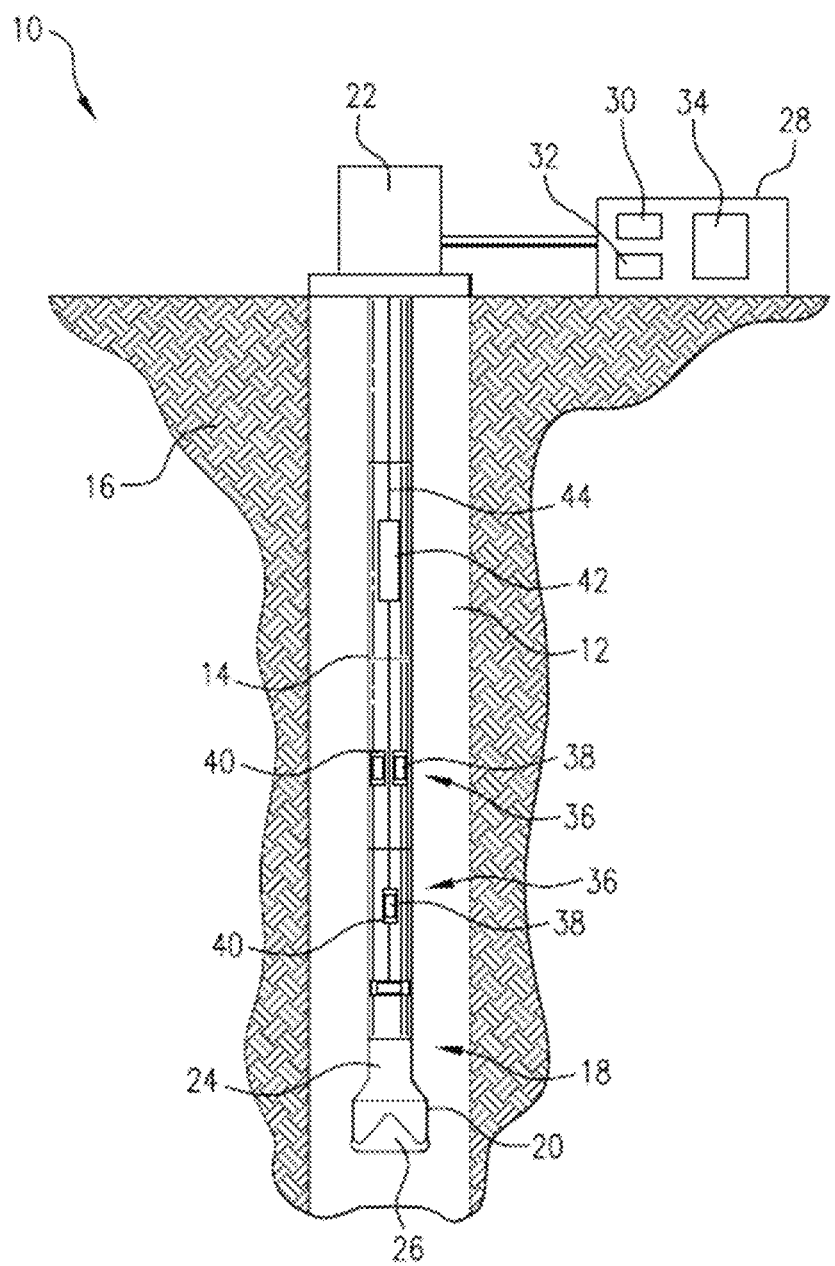
FIG. 1 is an exemplary embodiment of a drilling system including a drill string disposed in a borehole in an earth formation.

Referring to FIG. 1, an exemplary embodiment of a downhole drilling system 10 disposed in a borehole 12 is shown. A drill string 14 is disposed in the borehole 12, which penetrates at least one earth formation 16. Although the borehole 12 is shown in FIG. 1 to be of constant diameter, the borehole is not so limited. For example, the borehole 12 may be of varying diameter and/or direction (e.g., azimuth and inclination). The drill string 14 is made from, for example, a pipe or multiple pipe sections. The system 10 and/or the drill string 14 include a drilling assembly 18. Various measurement tools may also be incorporated into the system 10 to affect measurement regimes such as wireline measurement applications or logging-while-drilling (LWD) applications.

The drilling assembly 18, which may be configured as a bottomhole assembly (BHA), includes a drill bit 20 that is attached to the bottom end of the drill string 14 via various drilling assembly components. The drilling assembly 18 is configured to be conveyed into the borehole 12 from a drilling rig 22. The drilling assembly also includes various components for structural and operational support to the drill bit 20, such as a drill bit body 24 operably connected to cutters 26, a drilling motor (also referred to as a mud motor), and a stabilizer or reamer.

A processing unit 28 is connected in operable communication with the drilling assembly 18 and may be located, for example, at a surface location, a subsea location and/or a surface location on a marine well platform or a marine craft. The processing unit 28 may also be incorporated with the drill string 14 or the drilling assembly 18, or otherwise disposed downhole as desired. The processing unit 28 may be configured to perform functions such as controlling the drilling assembly 18, transmitting and receiving data and monitoring the drilling assembly 18 and the drill string 14. The processing unit 28, in one embodiment, includes a processor 30, a data storage device (or a computer-readable medium) 32 for storing, data, models and/or computer programs or software 34.

The system 10 also includes one or more measurement assemblies 36 for measuring forces experienced by the drill string while downhole and/or in operation. Each assembly 36 may be able to measure one or more of WOB, TOB and bending forces. As illustrated, each assembly includes a diode sensor 40 that may be disposed at any location along the length of a particular assembly 36. For simplicity, in FIG. 1 such assemblies are shown in the middle of assembly but can on the ends in one embodiment. The sensor, as described further below, may receive light from a light source such as a laser that is part of a light emitting assembly 38. Again, the relative positions of elements 38 and 40 can be varied depending on the context and as will be more fully described below.

The assembly 36 transmits signals to a processor in the form of, e.g., voltage changes, to a desired location. For example, the assemblies 36 may be coupled to a downhole electronics unit 42, which may receive signals from the assemblies 36 and transmit the data to a processing system such as the processing unit 28. Signals and data may be transmitted via any suitable transmission device or system, such as a cable 44. Other techniques used to transmit signals and data include wired pipe, electric and/or fiber optic connections, mud pulse, electromagnetic and acoustic telemetry.

The processing unit 28 is configured to analyze and/or transmit data to a user or other location for analysis. Such analysis includes estimating downhole parameters such as weight-on-bit (WOB), torque-on-bit (TOB) and bending forces on portions of the drill string 14 or bending forces on the bit (BOB). It shall be understood that in some embodiments, such processing may occur at processors other that at the surface including, for example, at the downhole electronics unit 44. In such a case, the results of the analysis may be transmitted to the surface processing unit 28 for further action/processing or may cause the drilling assembly 18 to operate in different manner automatically without input from the processing unit 28. Measurements of parameters such as torque, TOB, WOB and bending can also be used to estimate other parameters such as drill string direction or deviation, and unwanted deformation such as buckling. Although embodiments are described in conjunction with drill string and drilling operations, including logging-while-drilling (LWD) operations, they are not so limited. The apparatuses and methods described herein may be utilized with any component, including downhole components such as wireline tools that experience forces that need to be measured.

Figure 2:
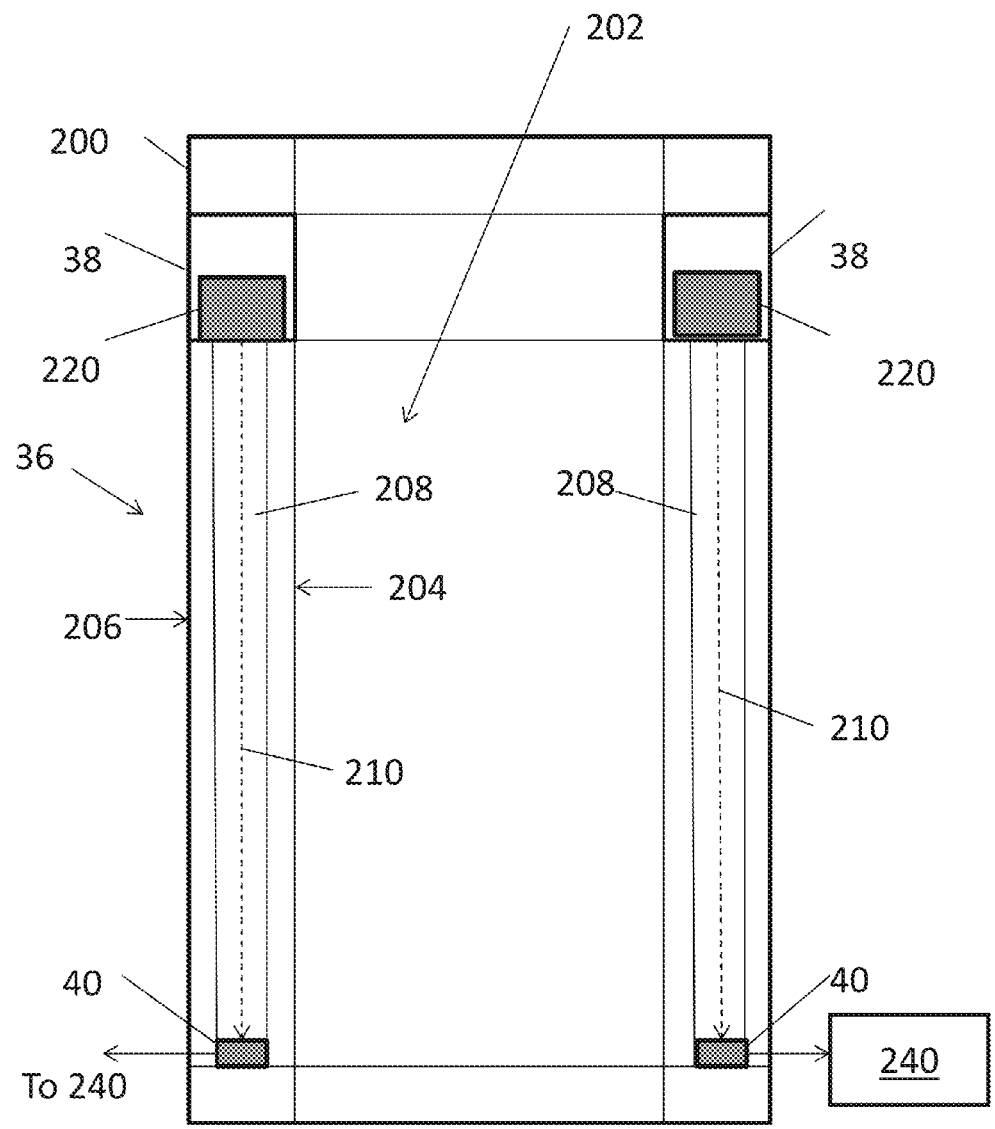
FIG. 2 is a cross-section view of a portion of the drill string of FIG. 1 including one or more sensor assemblies.

FIG. 2 illustrates a cross-section of an assembly 36 according to one embodiment. It shall be understood that the assembly 36 could be a measurement sub in one embodiment. The assembly 36 includes a body 200. The body 200 may be formed of any material and, in particular, a metal or other rigid material. In one embodiment, the body 200 is formed such that includes iron and may be formed of the same or similar materials that form a drill pipes of a drill string.

The body 200 includes inner wall 204 that defines an inner passageway or bore 202 through which a drilling fluid may pass during operation. While not illustrated, it shall be understood that the body 200 may include threads or other coupling elements that allow it to be connected to adjacent pipe segments, subs, or any other downhole implement including bottom hole assembly (BHA) components. The body 200 also includes an outer wall 206. One or more bores 208 is formed between the inner 204 and outer walls 206. As illustrated, the assembly includes 2 bores. It shall be understood that the assembly can include a single bore 208 in one embodiment and may include three bores or more bores 208 in another embodiment. Thus, while two bores 208 are shown, it shall be understood that one of them may be optional. As will be understood from the disclosure below, if only a single bore 208 is provided, the assembly may be able to determine one of TOB, WOB and bending. In the event that two are provided, two of TOB, WOB and bending may be measured. In the case where three are provided, all of TOB, WOB and bending may be measured.

As illustrated in FIG. 2, the assembly 36 includes a light emitting assembly 38 that generates a light beam 210. The light emitting assembly 38 includes a light source 220 that may be a laser or other source of light such as a diode. While two light sources are shown in FIG. 2, it could be understand that a single source of light could provide the light beams 210 in each bore 208. The light source 220 transmits the light to a sensor 40 that, in one embodiment is position sensitive element such as a photodiode sensor. In one embodiment, the photodiode sensor is a four quadrant photodiode or segmented photodiode sensor. The particular arrangement shown in FIG. 2 having the light source 220 and the sensor 40 at opposing ends of the bore 208 is utilized to measure one or both of TOB and bending forces. The laser light propagates parallel to the drill string axis and hits the segmented photodiodes in their respective centers if no forces are exerted on the drill string The sensors 40 provide voltage or other output signals 222 that indicate a location where the light beam 210 contacts the sensor 40. These signals can be provided to a processor 240 that may be part of the assembly 36 or may be located in a different location such as a BHA or a surface computer.

In particular, and as generally shown in FIGS. 3a and 3b, when torque is applied to the body 200 it will cause the location light beams contact the photo diodes. It shall be understood that the body 200 shown in FIGS. 3a and 3b is simplified and does not include bores 208 for clarity but that those bores are present.

As the torque is applied, the location where the light beam contacts the photodiodes moves. In FIG. 3a the location where the light beam 210 contacts the sensor when example torque 310 is applied is shown by solid circles 330. The dashed circles and cross indicate the edge location of sensors and a location where the center of the light beam 210 contacts the photodiode sensors when no forces are applied (e.g., a reference position). As torque is applied, the location of where the light beams 210 contacts their respective sensors generally rotates in the direction of the torque 310.

Consider an example where the body 200 is connected at or near a drill bit. As the top drive applies rotational motion to the drill string, when the bit is contacting rock, a torque in the direction of arrow 310 may be imparted on the body 200. This torque may cause the top 320 of the body 200 to rotate relative to the bottom 312 of the body. The amount of rotation (and thus, torque) may be determined by measuring the angular difference (a) between a reference orientation (340) and the rotated orientation (342). In FIG. 3a, the relative orientations are based on connecting the centers of the light spots (solid circles 370, 372) on each of the two sensors 350, 352 (shown generally as dashed circles) in the reference and rotated positions. Of course, if only a single light/sensor combination is used, the rotation could be determined based solely on the locational difference of the reference position and the rotated position. It shall be understood that the sensors may be able to determine a center of the light beams that hit it. An example of an equation that describes the measured rotation to an applied torque may take the form:

$$T = A\alpha; \quad (1)$$

where T is torque and A is a scaling constant that depends on the material forming the body. As will be understood, because the rotation is circular, if the spot moves to left on one sensor it will move the same amount to the right on another sensor. Thus, even if a bending occurs as described below, the angle α will remain constant.

Figure 4A:
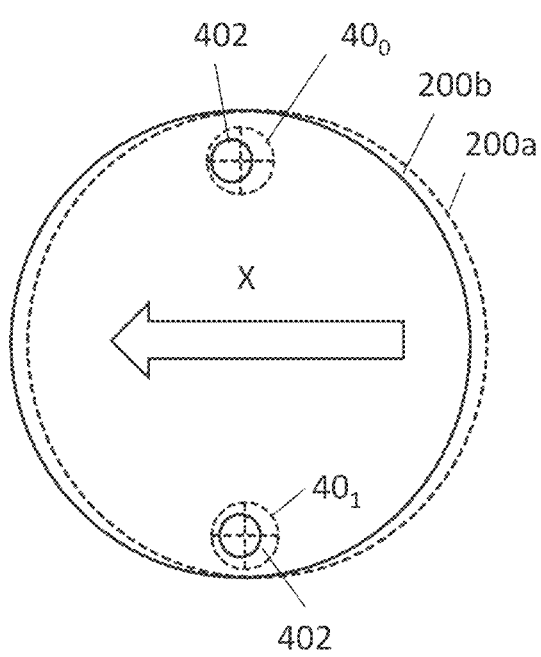
FIGS. 4a and 4b show from top view, respectively, the effect of x and y bending on light beam locations in an exemplary assembly of FIG. 2.
Figure 4B:
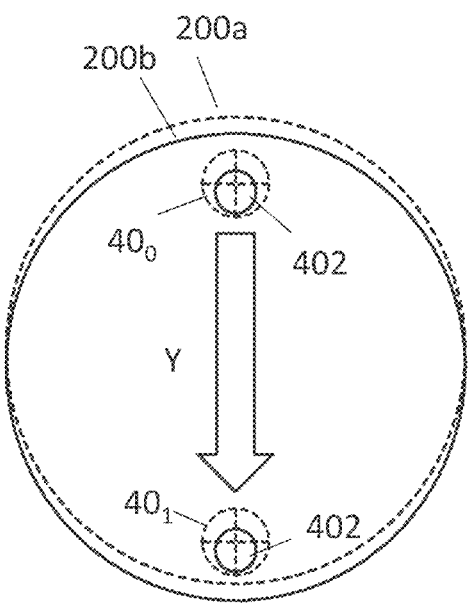

Similarly, and as shown in FIGS. 4a and 4b, as the body 200 is bent the x and y directions (see FIGS. 3a and 3b), the location on sensors 40 where the light beam hits will move. In FIG. 4a, as the body 200 is bent in the x direction, the light beam contact location (shown by circle 402) on the sensors 40 moves from the reference location linearly to the left. Herein the two sensors are labelled at $40_0$ and $40_1$ so that they can be referred to individually.

In FIG. 4a, as the body 200 is bent in the y direction, the light beam contact location (shown by circle 402) on the sensors 40 moves from the reference location linearly downward. Of course, the bending could include both x and y directions in one embodiment. This bending will cause the rotated center points due to torque described above to both move in the same direction and distance.

Figure 5:
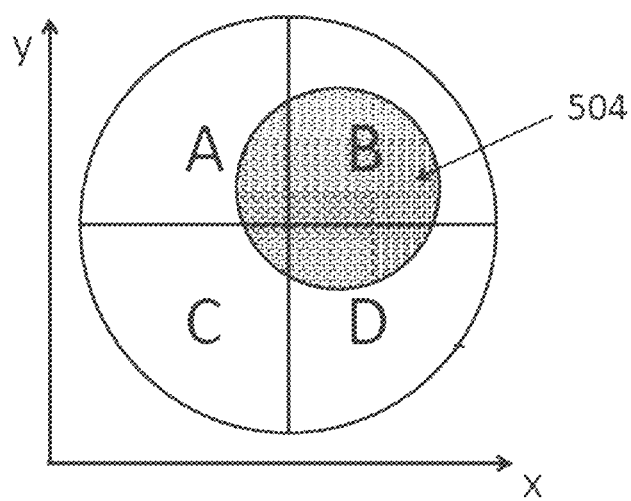
FIG. 5 shows an example of a 4 quadrant photosensor.

Consider a photodiode sensor 500 as shown in FIG. 5. The sensor 500 includes 4 quadrants A, B, C and D. The amount of energy received from the light beam contact location 504 in each quadrant can be represented by variables A, B, C, and D, respectively. The location in x and y may be determined as follows:

$$x = \frac{(A+C) - (B+D)}{(A+B+C+D)}; \text{ and} \quad (2)$$

$$y = \frac{(A+B) - (C+D)}{(A+B+C+D)}. \quad (3)$$

The above descriptions illustrate how bending and torque can cause the location where the light beams contact a photo diode can vary. It shall be understood that the variation due to torque and that due to bending can be separated from each other by a simple deconvolution algorithm, and torque and bending moments of the drill string can determined.

In particular, a reference (position r) location is measured and then compared to a later position (position m). In the reference position, on the first sensor ($40_0$) the reference position for the two sensors $40_0$ and $40_1$ is ($xr_0$, $yr_0$) and ($xr_1$, $yr_1$) respectively. Similarly, the measured positions are ($xm_0$, $ym_0$) and ($xm_1$, $ym_1$).

The rotation (e.g., torque) can be determined based on the location where the light dots 372, 370 contact the two sensors 40 according to:

$$\cos(\alpha) = \frac{\vec{Xr} \cdot \vec{Xm}}{|\vec{Xr}| \cdot |\vec{Xm}|}$$

were $\vec{Xr}$=($xr_1$−$xr_0$, $yr_1$−$yr_0$) and $\vec{Xm}$=($xm_1$−$xm_0$, $ym_1$−$ym_0$). Applying the dot product and absolute value to the above expands this to:

$$\cos(\alpha) = \frac{(xr1-xr0)(xm1-xm0) + (yr1-yr0)(ym1-ym0)}{\sqrt{(xr1-xr0)^2 + (yr1-yr0)^2} + \sqrt{(xm1-xm0)^2 + (ym1-ym0)^2}}$$

For bending, the x and y coordinates can be based off of how much in the x and y direction the points have move and a location of a center point (c; shown as (0,0) in FIG. 3). In particular:

$$\frac{x \text{ bending}}{y \text{ bending}} = (\vec{Xmc} - \vec{Xrc})$$

where C denotes the center location, and the vectors are the distance from the center between the points and $\vec{Xmc}$=1/2(xm0+xm1, ym0+ym1) and $\vec{Xrc}$=1/2 (xr0+xr1, yr0+yr1) which expands to:

$$\frac{x \text{ bending}}{y \text{ bending}} = \gamma \frac{1}{2} \frac{(xm0 - xro) + (xm1 - xr1)}{(ym0 - yr0) + (ym1 - yr1)}.$$

Figure 6:
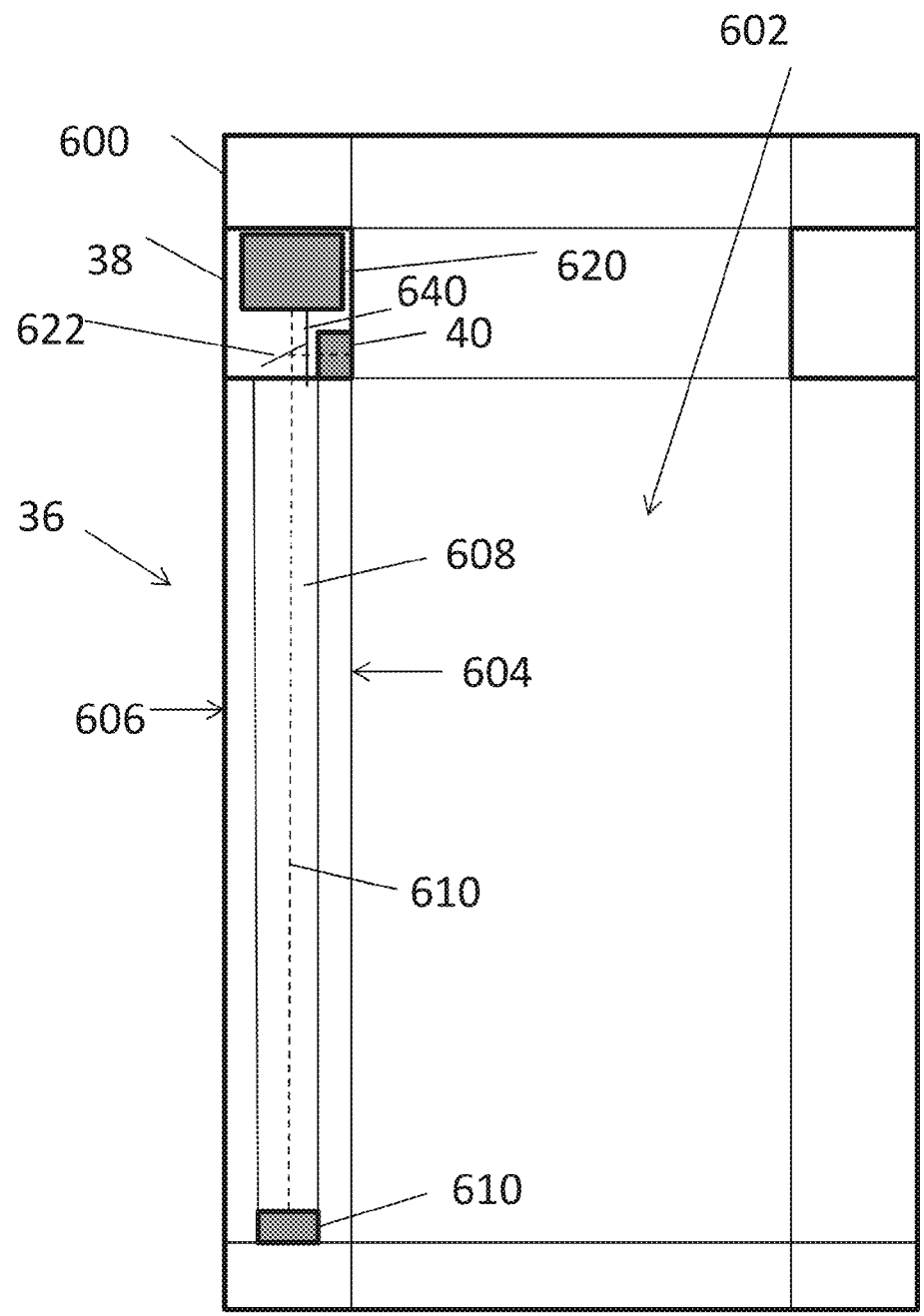
FIG. 6 shows a side view of weight on bit sensor assembly according to one embodiment.

FIG. 6 illustrates a cross-section of an assembly 36 according to one embodiment. This embodiment is used to measure weight on bit (WOB) and may be used alone or in combination with the above embodiments. That is, in one embodiment the assembly 36 shown in FIG. 5 may be part of one of the assemblies 36 described above. In another embodiment, it is a stand alone assembly.

The illustrate assembly 36 could be a measurement sub in one embodiment. The assembly 36 includes a body 600. The body 600 may be formed of any material and, in particular, a metal or other rigid material. In one embodiment, the body 600 is formed such that includes iron and may be formed of the same or similar materials that form a drill pipes of a drill string.

The body 600 includes inner wall 604 that defines an inner passageway or bore 602 through which a drilling fluid may pass during operation. While not illustrated, it shall be understood that the body 600 may include threads or other coupling elements that allow it to be connected to adjacent pipe segments, subs, or any other downhole implement including bottom hole assembly (BHA) components. The body 600 also includes an outer wall 606. One or more bores 608 is formed between the inner 604 and outer walls 606. As illustrated, the assembly includes a single bore. As will be understood, the single bore could be offset from the other bores described above in the event that this embodiment is included in a single assembly with those described above.

As illustrated in FIG. 6, the assembly 36 includes a light emitting assembly 38 that generates a light beam 610. The light emitting assembly 38 includes a light source 620 that may be a laser or other source of light such as a diode. The light source 620 transmits the light through bore 608 to a mirror 610. The light is reflected back from the mirror 610 and a beam splitter 622 guides the reflected light towards sensor 40 that, in one embodiment is a photodiode sensor. A wall 640 with a slit 642 (FIG. 6) may be interposed between the beam splitter 622 and the sensor 40. The wall 640, beam splitter 622 and sensor 40 form a sensor assembly 660 that may be included in the light emitting assembly 38. Of course, it may be outside of that assembly in one embodiment.

Figure 7:
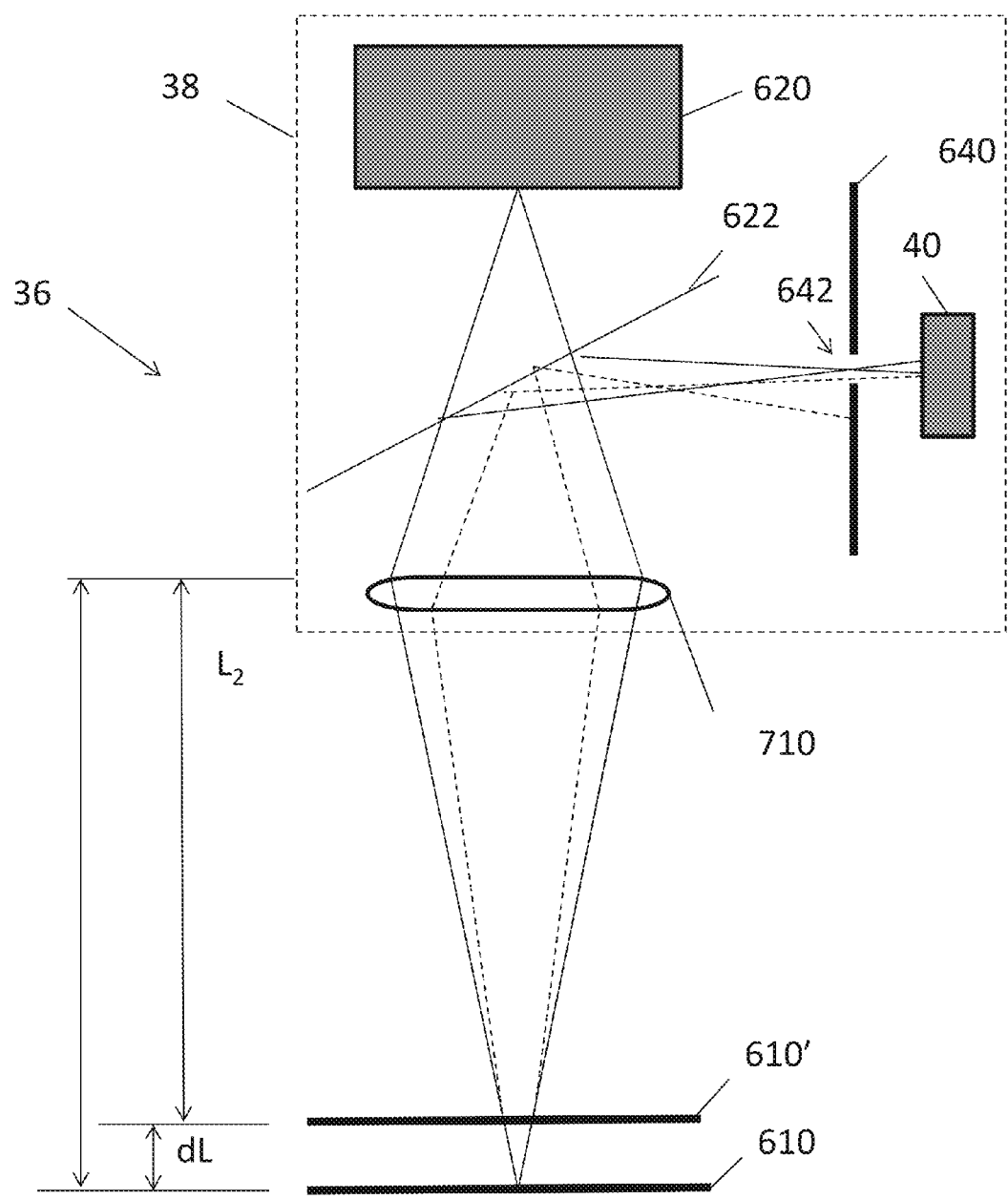
FIG. 7 shows a simplified block diagram and a theory of operation for the assembly of FIG. 6.

FIG. 7 shows a simplified example of the assembly 36 of FIG. 6 shown in a manner that allows for the theory of operation of the embodiment of FIG. 6 to be more easily understood. In general, variations in WOB will change the distance from the light emitting assembly 38 to the mirror 610. As illustrated, the mirror is shown in a first position that is a distance $L_1$ from the light source 38. The exact location in the assembly 38 from which $L_1$ is measured can be varied. As the pipe is compressed due to increased weight on the bit, the mirror may move closer as indicated by mirror 610' that is a different distance $L_2$ from the light emitting assembly 38. The difference in distance is shown as dL. As illustrated, the transmitted and reflected beams when the mirror 610 is in first position are shown by solid lines. The beam splitter 622 may be sized and arranged such it focuses the reflected beams through the slit 642 in the wall 640 to allow for maximum light transmission to the sensor 40. When the mirror 610' is in the second position, the splitter 622 will cause less of the light to pass through the slit 642 and, thus, the intensity of the signal measured by sensor 40 will decrease. As will be understood, WOB is proportional to dL.

In FIG. 6 the light is shown as dispersing as it leaves light source 620. In one embodiment, the light source 620 produces non-coherent or non-collimated light. In one embodiment, the light may be produced by a diode and may include a single or multiple frequencies. A lens 710 may optionally be provided to focus the light on to the sensor 610. As the sensor location moves (e.g., compare 610 and 610") the light becomes unfocused and the reflected light patterns change. As such, the amount of light the beam splitter 622 causes to pass through the slit 642 will vary as described above.

Generally, some of the teachings herein are reduced to an algorithm that is stored on machine-readable media. The algorithm is implemented by the computer processing system and provides operators with desired output.

In support of the teachings herein, various analysis components may be used, including digital and/or analog systems. The digital and/or analog systems may be included, for example, in the downhole electronics unit 42 or the processing unit 28. The systems may include components such as a processor, analog to digital converter, digital to analog converter, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs, USB flash drives, removable storage devices), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for determining torque on bit and bending forces in a drilling assembly, the apparatus including:
   a body having an inner bore defined by an inner wall and having an outer wall, the body also including first and second light bores disposed between the inner wall and the outer wall;
   a light emitting assembly arranged and configured to cause a light beam to enter the first and second light bores; and
   first and second light sensors disposed in or at an end of the first and second light bores, respectively, that measure a location where light that enters the first and second light bores contacts the sensors.

2. The apparatus of claim 1, wherein the light emitting assembly includes a light emitting diode.

3. The apparatus of claim 1, wherein the light emitting assembly includes a laser.

4. The apparatus of claim 1, further comprising;
   a controller that receives signals form the first and second light sensors indicative of where the light contacts the sensors.

5. The apparatus of claim 1, wherein the controller is configured determine a torque experienced by the body based on rotation of where the light contacts the sensors as compared to an initial location.

6. The apparatus of claim 5, wherein the controller is configured determine a bending force experience by the body based on translation of where the light contacts the sensors as compared to an initial location.

7. The apparatus of claim 1, wherein the controller is configured determine a bending force experience by the body based on translation of where the light contacts the sensors as compared to an initial location.

8. The apparatus of claim 1, wherein one of the first and second light sensors is a four quadrant photodiode or a segmented photodiode sensor.

9. A method form measuring, while drilling torque on bit and bending forces in a drilling assembly, the method including:
   providing light beams through at least a portion of first and second light bores in a body having an inner bore defined by an inner wall and having an outer wall, the first and second light bores formed between the inner wall and the outer wall;
   sensing a location on sensors disposed in or at an end of the first and second light bores, respectively, where light that enters the first and second light bores contacts the sensors; and
   comparing the sensed locations with reference locations to determine at least one of torque on bit and bending forces in the assembly.

10. The method of claim 9, wherein the light beams are formed by a laser.

11. The method of claim 9, wherein the light beams are formed by a light emitting diode.

12. The method of claim 9, wherein comparing includes determining a torque experienced by the body based on rotation of the sensed location as compared to the reference locations.

13. The method of claim 12, wherein comparing includes determining a bending force experienced by the body based on translation of the sensed location as compared to the reference locations.

14. The method of claim 9, wherein comparing includes determining a bending force experienced by the body based on translation of the sensed location as compared to the reference locations.

15. An apparatus for determining weight on bit in a drilling assembly, the apparatus including:
- a body having an inner bore defined by an inner wall and having an outer wall, the body also including a light bore disposed between the inner wall and the outer wall;
- a light emitting assembly that includes a light source, a sensor, a beam splitter, and a wall having a slit disposed between the light source and the sensor, the light emitting assembly arranged and configured to cause a light beam to enter the light bore; and
- a mirror disposed in or at an end of the light bore that reflects light back into the light emitting assembly;
- wherein the beam splitter causes a portion of the reflected light to be directed towards the slit in the wall to contact the sensor.

16. The apparatus of claim 15, wherein an amount of light sensed by the sensor is used to determine an amount of compression of the body to determine the weight on bit.

17. The apparatus of claim 15, further comprising a lens that focuses the light beam on the mirror.

18. The apparatus of claim 15, wherein the sensor is a photodiode sensor.

19. The apparatus of claim 15, wherein the light source produces non-collimated light.

20. The apparatus of claim 15, wherein the light source produces non-coherent light.

* * * * *